US008106094B2

(12) United States Patent
Sah et al.

(10) Patent No.: US 8,106,094 B2
(45) Date of Patent: *Jan. 31, 2012

(54) COMPOSITIONS AND METHODS FOR TREATING SKIN CONDITIONS

(75) Inventors: Archana Sah, Redmond, WA (US); Victoria Dole, Whitehouse Station, NJ (US); Glenn Nystrand, Lebanon, NJ (US); Miri Seiberg, Princeton, NJ (US); Jue-Chen Liu, Belle Mead, NJ (US); Ellen Kurtz, Ringoes, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 789 days.

This patent is subject to a terminal disclaimer.

(21) Appl. No.: 10/903,702

(22) Filed: Jul. 30, 2004

(65) Prior Publication Data
US 2005/0036963 A1    Feb. 17, 2005

Related U.S. Application Data

(63) Continuation-in-part of application No. 09/110,409, filed on Jul. 6, 1998, now Pat. No. 8,039,026, and a continuation-in-part of application No. 09/698,454, filed on Oct. 27, 2000.

(51) Int. Cl.
*A01N 37/00* (2006.01)
*A61K 31/20* (2006.01)
*A61K 31/04* (2006.01)

(52) U.S. Cl. .......................... 514/559; 514/725
(58) Field of Classification Search .................. 514/559, 514/725
See application file for complete search history.

(56) References Cited

U.S. PATENT DOCUMENTS

| | | | |
|---|---|---|---|
| 2,876,164 A | 3/1959 | Wershaw | |
| 2,924,525 A | 2/1960 | Kruse et al. | |
| 3,097,947 A | 7/1963 | Kemmerer | |
| 3,625,976 A | 12/1971 | Theimer | |
| 3,755,560 A | 8/1973 | Dickert | |
| 3,856,934 A * | 12/1974 | Kligman | 424/62 |
| 3,865,933 A * | 2/1975 | Mudge | 424/677 |
| 4,007,266 A | 2/1977 | Choay | |
| 4,056,637 A | 11/1977 | Hagiwara et al. | |
| 4,151,304 A | 4/1979 | Evans | |
| 4,190,671 A | 2/1980 | Vanstone | |
| 4,219,569 A | 8/1980 | Glenn | |
| 4,223,018 A | 9/1980 | Belle | |
| 4,254,105 A | 3/1981 | Fukuda | |
| 4,272,544 A | 6/1981 | Cella | |
| 4,278,570 A | 7/1981 | Flom | |
| 4,279,930 A | 7/1981 | Hall | |
| 4,297,348 A | 10/1981 | Frazier | |
| 4,331,692 A | 5/1982 | Drevici | |
| 4,333,927 A | 6/1982 | Ofuchi | |
| 4,368,187 A | 1/1983 | Flom | |
| 4,370,315 A | 1/1983 | Greff | |
| 4,382,960 A | 5/1983 | Flom | |
| 4,386,067 A | 5/1983 | Guillon | |
| 4,386,104 A * | 5/1983 | Nazzaro-Porro | 514/558 |
| 4,421,769 A | 12/1983 | Dixon | |
| 4,427,670 A | 1/1984 | Ofuchi | |
| 4,434,095 A | 2/1984 | Chipens et al. | |
| 4,437,895 A | 3/1984 | Koulbanis | |
| 4,439,418 A | 3/1984 | Moller | |
| 4,462,981 A | 7/1984 | Smith | |
| 4,477,434 A | 10/1984 | Kosaka | |
| 4,486,448 A | 12/1984 | Ser | |
| 4,488,564 A | 12/1984 | Grollier | |
| 4,512,973 A | 4/1985 | Dennis | |
| 4,515,778 A | 5/1985 | Kastell | |
| 4,524,067 A * | 6/1985 | Arichi et al. | 514/33 |
| 4,537,782 A | 8/1985 | Millet | |
| 4,550,035 A | 10/1985 | Smith | |
| 4,578,267 A | 3/1986 | Salamone | |
| 4,584,190 A | 4/1986 | Tejima | |
| 4,603,146 A | 7/1986 | Kligman | |
| 4,604,281 A | 8/1986 | Deckner | |
| 4,612,192 A | 9/1986 | Scheuffgen | |
| 4,690,821 A | 9/1987 | Smith | |
| 4,707,293 A | 11/1987 | Ferro | |
| 4,727,088 A | 2/1988 | Scott et al. | |
| 4,760,096 A | 7/1988 | Sakai | |
| 4,793,991 A | 12/1988 | Slimak | |
| 4,824,662 A | 4/1989 | Hofmann | |
| 4,834,076 A | 5/1989 | Millet | |
| 4,847,267 A | 7/1989 | Deckner | |
| 4,851,214 A | 7/1989 | Walters | |
| 4,859,458 A | 8/1989 | Salamone | |
| 4,867,964 A | 9/1989 | Forestier | |
| 4,871,530 A | 10/1989 | Grollier | |
| 4,885,169 A | 12/1989 | Gazzani | |

(Continued)

FOREIGN PATENT DOCUMENTS

AU    724988 B2    5/1998

(Continued)

OTHER PUBLICATIONS

Terzioglu et al., The Internet Journal of Alternative Medicine, 7 pages (1996).*
Parellada et al. J. Nat. Prod. 1995, 58(6). Abstract Only 2 pages.*
International Legume Database and information enclosed, http://www.lidis.org, 4 pages (1999).*
Izumi et al. Phytochemistry 42(2) (1996) 309-312.*
"A Combined Soybean Crushing-Deordorizing System that Yields 100-200 Mesh Powder for Food Additive Use has been Developed by Shinyu Zoki Co. Ltd. and Mitsubishi Rayon Engineering Ltd.", *Tech Times*, pp. 10 (1978).

(Continued)

*Primary Examiner* — Brandon Fetterolf
*Assistant Examiner* — Shirley V Gembeh

(57) ABSTRACT

This invention relates to methods and compositions for treating and ameliorating skin conditions including post inflammatory hyperpigmentation (PIH). More particularly, this invention relates to compositions containing certain natural extracts, salicylic acid, and natural or synthetic retinoids. The composition was clinically proven to reduce PIH.

13 Claims, No Drawings

U.S. PATENT DOCUMENTS

| | | |
|---|---|---|
| 4,895,839 A | 1/1990 | Bombardelli |
| 4,906,457 A | 3/1990 | Ryan |
| 4,943,462 A | 7/1990 | Komerska |
| 4,960,588 A | 10/1990 | Hoshowski |
| 4,960,764 A | 10/1990 | Figueroa |
| 4,970,216 A | 11/1990 | Deckner |
| 4,971,825 A | 11/1990 | Kitazume et al. |
| 4,978,528 A | 12/1990 | Degre |
| 5,002,761 A | 3/1991 | Mueller |
| 5,006,337 A | 4/1991 | Motitschke et al. |
| 5,032,382 A | 7/1991 | Crollie |
| 5,032,400 A | 7/1991 | Wiersum |
| 5,043,323 A | 8/1991 | Bombardelli |
| 5,057,417 A | 10/1991 | Hammonds et al. |
| 5,077,038 A | 12/1991 | Hofmann |
| 5,077,040 A | 12/1991 | Bergmann |
| 5,104,655 A | 4/1992 | Bombardelli |
| 5,110,603 A | 5/1992 | Rau |
| 5,116,605 A | 5/1992 | Alt |
| 5,118,671 A | 6/1992 | Bombardelli |
| 5,130,142 A | 7/1992 | Wong et al. |
| 5,147,859 A | 9/1992 | Bombardelli |
| 5,166,139 A | 11/1992 | Bombardelli |
| 5,171,577 A | 12/1992 | Griat |
| 5,179,091 A | 1/1993 | Lesieur |
| 5,188,823 A | 2/1993 | Shapiro |
| 5,192,332 A | 3/1993 | Lang |
| 5,194,252 A | 3/1993 | Hofmann |
| 5,217,717 A | 6/1993 | Kennedy |
| 5,229,104 A | 7/1993 | Sottery |
| 5,231,090 A | 7/1993 | Hsia |
| 5,248,495 A | 9/1993 | Patterson |
| 5,254,331 A | 10/1993 | Mausner |
| 5,260,065 A | 11/1993 | Mathur |
| 5,270,042 A | 12/1993 | Whitham |
| 5,276,058 A | 1/1994 | Satoh |
| 5,306,444 A | 4/1994 | Kitamura |
| 5,310,734 A | 5/1994 | Losch |
| 5,322,839 A | 6/1994 | Voegeli |
| 5,352,443 A | 10/1994 | Kubo |
| 5,362,494 A | 11/1994 | Zysman |
| 5,364,886 A | 11/1994 | Loliger |
| 5,393,519 A | 2/1995 | Dowell |
| 5,397,497 A | 3/1995 | Jakobson |
| 5,407,675 A | 4/1995 | Etemad-Moghadam |
| 5,411,742 A | 5/1995 | Sebag |
| 5,427,814 A | 6/1995 | Loliger |
| 5,428,026 A | 6/1995 | Colarow |
| 5,438,044 A | 8/1995 | Losch |
| 5,439,672 A | 8/1995 | Zabotto |
| 5,443,839 A | 8/1995 | Meybeck |
| 5,443,840 A | 8/1995 | Morancais |
| 5,444,092 A | 8/1995 | Collins |
| 5,446,605 A | 8/1995 | Umehara |
| 5,466,452 A | 11/1995 | Whittle |
| 5,468,473 A | 11/1995 | Mullen |
| 5,498,420 A | 3/1996 | Mentrup Edgar |
| 5,503,832 A | 4/1996 | De Stoutz |
| 5,505,946 A | 4/1996 | Kennedy et al. |
| 5,510,391 A | 4/1996 | Elson |
| 5,523,308 A | 6/1996 | Costanzo |
| 5,539,129 A | 7/1996 | Zysman |
| 5,545,399 A | 8/1996 | Lee |
| 5,547,661 A | 8/1996 | Sun |
| 5,554,647 A | 9/1996 | Perricone |
| 5,565,439 A | 10/1996 | Piazza et al. |
| 5,565,493 A | 10/1996 | Nakata et al. |
| 5,567,420 A | 10/1996 | McEleney |
| 5,569,663 A | 10/1996 | Ribier |
| 5,571,503 A | 11/1996 | Mausner |
| 5,578,297 A | 11/1996 | Mellul |
| 5,589,181 A | 12/1996 | Bencsits |
| 5,595,984 A | 1/1997 | Blank |
| 5,597,814 A | 1/1997 | Blank |
| 5,601,833 A | 2/1997 | Roboer |
| 5,603,949 A | 2/1997 | Meybeck |
| 5,605,894 A | 2/1997 | Blank |
| 5,607,666 A | 3/1997 | Masson |
| 5,607,692 A | 3/1997 | Ribier |
| 5,614,180 A | 3/1997 | Chung |
| 5,614,215 A | 3/1997 | Ribier |
| 5,616,572 A | 4/1997 | Blank |
| 5,618,522 A | 4/1997 | Kaleta |
| 5,620,692 A | 4/1997 | Potter |
| 5,622,690 A | 4/1997 | Potter |
| 5,626,868 A | 5/1997 | Morancais |
| 5,629,015 A | 5/1997 | Ribier |
| 5,629,301 A | 5/1997 | Blank |
| 5,631,318 A | 5/1997 | Ito |
| 5,635,165 A | 6/1997 | Panitch |
| 5,637,316 A | 6/1997 | Ribier |
| 5,639,785 A | 6/1997 | Kung |
| 5,641,509 A | 6/1997 | Gross |
| 5,643,583 A | 7/1997 | Voultoury |
| 5,643,587 A | 7/1997 | Scancarella |
| 5,643,601 A | 7/1997 | Gross |
| 5,650,166 A | 7/1997 | Ribier |
| 5,652,230 A | 7/1997 | Blank |
| 5,653,988 A | 8/1997 | Gerber |
| 5,660,853 A | 8/1997 | Hansenne-Richoux |
| 5,665,367 A | 9/1997 | Burger |
| 5,670,547 A | 9/1997 | Milstein et al. |
| 5,674,511 A | 10/1997 | Kacher |
| 5,676,935 A | 10/1997 | Mellul |
| 5,676,956 A | 10/1997 | Duffy |
| 5,679,374 A | 10/1997 | Fanchon |
| 5,681,571 A | 10/1997 | Homgren et al. |
| 5,681,852 A | 10/1997 | Bissett |
| 5,683,683 A | 11/1997 | Scafidi |
| 5,686,102 A | 11/1997 | Gross |
| 5,688,763 A | 11/1997 | Hammonds, Jr. et al. |
| 5,691,327 A | 11/1997 | Blank |
| 5,712,356 A | 1/1998 | Bothe et al. |
| 5,723,148 A | 3/1998 | Love |
| 5,741,496 A | 4/1998 | Khaiat |
| 5,753,612 A | 5/1998 | Mitrani |
| 5,755,814 A | 5/1998 | Berg |
| 5,762,916 A | 6/1998 | Ansmann |
| 5,766,628 A | 6/1998 | Nurnberg |
| 5,776,917 A | 7/1998 | Blank |
| 5,780,456 A | 7/1998 | Blank |
| 5,780,457 A | 7/1998 | Blank |
| 5,780,458 A | 7/1998 | Blank |
| 5,780,459 A | 7/1998 | Blank |
| 5,786,345 A | 7/1998 | Blank |
| 5,786,346 A | 7/1998 | Blank |
| 5,789,396 A | 8/1998 | Blank |
| 5,795,879 A | 8/1998 | Blank |
| 5,801,163 A | 9/1998 | Blank |
| 5,804,216 A | 9/1998 | Terren |
| 5,807,545 A | 9/1998 | Coffindaffer |
| 5,824,702 A | 10/1998 | Wei |
| 5,833,965 A | 11/1998 | Sun |
| 5,834,013 A | 11/1998 | Ribier |
| 5,834,513 A | 11/1998 | Ptchelintsev |
| 5,840,717 A | 11/1998 | Blank |
| 5,843,907 A | 12/1998 | Sakai et al. |
| 5,843,926 A | 12/1998 | Blank |
| 5,863,546 A | 1/1999 | Swinehart |
| 5,869,031 A | 2/1999 | Tarroux et al. |
| 5,869,470 A | 2/1999 | Blank |
| 5,871,743 A * | 2/1999 | Chajuss ..................... 424/757 |
| 5,871,823 A | 2/1999 | Anders et al. |
| 5,880,314 A | 3/1999 | Shinomiya |
| 5,885,593 A | 3/1999 | Epstein |
| 5,885,596 A | 3/1999 | Parab |
| 5,885,600 A | 3/1999 | Blum |
| 5,885,617 A | 3/1999 | Jordan |
| 5,885,948 A | 3/1999 | Glenn |
| 5,888,522 A | 3/1999 | Pickart |
| 5,908,618 A | 6/1999 | Lorant |
| 5,912,175 A | 6/1999 | Wille, Jr. |
| 5,916,577 A | 6/1999 | Golz |
| 5,928,654 A | 7/1999 | Duranton |
| 5,928,658 A | 7/1999 | Kishida |
| 5,928,889 A | 7/1999 | Bakich |
| 5,936,052 A | 8/1999 | Bothe et al. |

| Patent Number | Kind | Date | Inventor |
|---|---|---|---|
| 5,942,479 | A | 8/1999 | Frankenback |
| 5,945,095 | A | 8/1999 | Mougin |
| 5,945,109 | A | 8/1999 | Schmidt |
| 5,952,373 | A | 9/1999 | Lanzendorfer |
| 5,958,387 | A | 9/1999 | Bara |
| 5,961,980 | A | 10/1999 | Kennedy |
| 5,962,015 | A | 10/1999 | Delrieu |
| 5,962,441 | A | 10/1999 | Blank |
| 5,965,153 | A | 10/1999 | Allen |
| 5,972,355 | A | 10/1999 | Knight et al. |
| 5,981,450 | A | 11/1999 | Fabry |
| 5,985,338 | A | 11/1999 | Suh |
| 5,985,809 | A | 11/1999 | Frankenback |
| 5,990,291 | A | 11/1999 | Waggle |
| 6,004,915 | A | 12/1999 | Elliott |
| 6,013,250 | A | 1/2000 | Cannell |
| 6,013,255 | A | 1/2000 | Edens |
| 6,017,549 | A | 1/2000 | Knight et al. |
| 6,017,893 | A | 1/2000 | Segelman |
| 6,018,001 | A | 1/2000 | Hiratani et al. |
| 6,019,962 | A | 2/2000 | Rabe |
| 6,030,931 | A | 2/2000 | Vinski |
| 6,033,680 | A | 3/2000 | Dixon |
| 6,045,779 | A | 4/2000 | Mueller |
| 6,048,520 | A | 4/2000 | Hoshowski |
| 6,051,602 | A | 4/2000 | Bissett |
| 6,054,137 | A * | 4/2000 | Breton et al. .............. 424/400 |
| 6,060,070 | A | 5/2000 | Gorbach |
| 6,063,398 | A | 5/2000 | Gueret |
| 6,080,393 | A | 6/2000 | Liu et al. |
| 6,093,411 | A | 7/2000 | Bissett |
| 6,096,327 | A | 8/2000 | Lezdey et al. |
| 6,126,933 | A | 10/2000 | Warne et al. |
| 6,146,645 | A * | 11/2000 | Deckers et al. ............ 424/401 |
| 6,180,662 | B1 | 1/2001 | Lanzendorfer |
| 6,183,761 | B1 | 2/2001 | Bissett |
| 6,183,762 | B1 | 2/2001 | Deckers et al. |
| 6,248,350 | B1 | 6/2001 | Mori et al. |
| 6,261,603 | B1 | 7/2001 | McElwain |
| 6,323,219 | B1 * | 11/2001 | Costanzo .................. 514/317 |
| 6,348,200 | B1 * | 2/2002 | Nakajima et al. ........... 424/401 |
| 6,399,083 | B1 | 6/2002 | Pillai et al. |
| 6,423,747 | B1 | 7/2002 | Lanzendörfer |
| 6,433,025 | B1 | 8/2002 | Lorenz |
| 6,447,809 | B1 | 9/2002 | Krumhar et al. |
| 6,461,627 | B1 | 10/2002 | Ichioka |
| 6,551,606 | B1 | 4/2003 | Golz-Berner et al. |
| 6,555,143 | B2 | 4/2003 | Miller et al. |
| 6,558,656 | B2 | 5/2003 | Mann |
| 6,638,543 | B2 | 10/2003 | Kang et al. |
| 2001/0012853 | A1 * | 8/2001 | Bissett .................... 514/456 |
| 2002/0034489 | A1 | 3/2002 | Wiegland |
| 2002/0035046 | A1 | 3/2002 | Lukenbach |
| 2002/0065300 | A1 * | 5/2002 | Seiberg et al. ............. 514/317 |
| 2002/0160061 | A1 | 10/2002 | Saliou et al. |
| 2002/0160062 | A1 | 10/2002 | Liu et al. |
| 2002/0160063 | A1 | 10/2002 | Miller et al. |
| 2002/0182166 | A1 | 12/2002 | Martin |
| 2002/0192313 | A1 | 12/2002 | Saliou et al. |
| 2002/0197244 | A1 | 12/2002 | Seiberg et al. |
| 2003/0064048 | A1 | 4/2003 | Seiberg et al. |
| 2003/0064049 | A1 | 4/2003 | Seiberg et al. |
| 2003/0224075 | A1 | 12/2003 | Liu et al. |
| 2004/0009142 | A1 | 1/2004 | Zambaux |
| 2004/0062731 | A1 | 4/2004 | Seiberg et al. |
| 2004/0063593 | A1 | 4/2004 | Wu et al. |
| 2004/0067244 | A1 | 4/2004 | Friedman |
| 2005/0008665 | A1 | 1/2005 | Batzer |
| 2005/0019279 | A1 | 1/2005 | Goppel |
| 2005/0281776 | A1 | 12/2005 | Courcoux |
| 2007/0009459 | A1 | 1/2007 | Magnant |
| 2007/0041931 | A1 | 2/2007 | Morelli |
| 2007/0160564 | A1 | 7/2007 | Liu et al. |

FOREIGN PATENT DOCUMENTS

| | | | |
|---|---|---|---|
| CN | 1081899 | A | 2/1994 |
| CN | 1094279 | A | 11/1994 |
| CN | 1146876 | A | 4/1997 |
| CN | 1166960 | A | 12/1997 |
| DE | 4432947 | A | 3/1996 |
| DE | 19634206 | A | 3/1998 |
| DE | 19818849 | A | 10/1998 |
| EP | 0 273 202 | A2 | 7/1988 |
| EP | 0 341 745 | A1 | 11/1989 |
| EP | 0 393 532 | A2 | 10/1990 |
| EP | 0 421 021 | A1 | 4/1991 |
| EP | 0 473 502 | A1 | 3/1992 |
| EP | 0 476 311 | A1 | 3/1992 |
| EP | 0 508 886 | A1 | 10/1992 |
| EP | 0 532 465 | A | 3/1993 |
| EP | 0 574 352 | A1 | 12/1993 |
| EP | 0 581 624 | A1 | 2/1994 |
| EP | 0 581 624 | B1 | 2/1994 |
| EP | 0 582 239 | A1 | 2/1994 |
| EP | 0 582 239 | B1 | 2/1994 |
| EP | 0 643 083 | A1 | 3/1995 |
| EP | 0 643 960 | A1 | 3/1995 |
| EP | 0 655 470 | A1 | 5/1995 |
| EP | 0 661 037 | A1 | 7/1995 |
| EP | 0 707 851 | A2 | 4/1996 |
| EP | 0 713 106 | A1 | 5/1996 |
| EP | 0 758 687 | A1 | 2/1997 |
| EP | 0 774 249 | A2 | 5/1997 |
| EP | 0 811 595 | A1 | 12/1997 |
| EP | 0 814 116 | A1 | 12/1997 |
| EP | 0 963 761 | A1 | 12/1999 |
| EP | 1 074 240 | A2 | 2/2001 |
| EP | 1 077 063 | A2 | 2/2001 |
| EP | 1 192 938 | A2 | 4/2002 |
| EP | 1 210 946 | A | 6/2002 |
| EP | 1 236 402 | A1 | 9/2002 |
| EP | 1 236 465 | A2 | 9/2002 |
| EP | 1 348 441 | A | 10/2003 |
| EP | 1 647 278 | A | 4/2006 |
| FR | 2 596 986 | A1 | 10/1987 |
| FR | 2 641 696 | A1 | 7/1990 |
| FR | 2 685 202 | A1 | 6/1993 |
| FR | 2 803 747 | A | 7/2001 |
| FR | 2 811 226 | A1 | 1/2002 |
| GB | 1098951 | A | 1/1968 |
| JP | 58225003 | A | 12/1983 |
| JP | 58225004 | A | 12/1983 |
| JP | 59187756 | A | 10/1984 |
| JP | 60061513 | A | 4/1985 |
| JP | 62036304 | A | 2/1987 |
| JP | 63068512 | A | 3/1988 |
| JP | 63096120 | A | 4/1988 |
| JP | 63135310 | A | 6/1988 |
| JP | 63227515 | A | 9/1988 |
| JP | 63316711 | A | 12/1988 |
| JP | 1093519 | A | 4/1989 |
| JP | 1096106 | A | 4/1989 |
| JP | 02-286165 | A | 11/1990 |
| JP | 3127713 | A | 5/1991 |
| JP | 4169514 | A | 6/1992 |
| JP | 04283518 | A | 10/1992 |
| JP | 5015574 | A | 1/1993 |
| JP | 5114905 | A | 5/1993 |
| JP | 5213729 | A | 8/1993 |
| JP | 5246932 | A | 9/1993 |
| JP | 5320024 | A | 12/1993 |
| JP | 5320061 | A | 12/1993 |
| JP | 6145061 | A | 5/1994 |
| JP | 6192085 | A | 7/1994 |
| JP | 06256156 | A | 9/1994 |
| JP | 6256156 | A | 9/1994 |
| JP | 7010772 | A | 1/1995 |
| JP | 7196527 | A | 8/1995 |
| JP | 7196529 | A | 8/1995 |
| JP | 7304655 | A | 11/1995 |
| JP | 8012560 | A | 1/1996 |
| JP | 8020597 | A | 1/1996 |
| JP | 8040824 | A | 2/1996 |
| JP | 8059450 | A | 3/1996 |
| JP | 8099891 | A | 4/1996 |
| JP | 08143442 | | * 6/1996 |
| JP | 8143442 | A | 6/1996 |
| JP | 8333260 | A | 12/1996 |

| | | | |
|---|---|---|---|
| JP | 9025212 A | 1/1997 |
| JP | 9025213 A | 1/1997 |
| JP | 9025214 A | 1/1997 |
| JP | 9059166 A | 3/1997 |
| JP | 9077638 A | 3/1997 |
| JP | 9176033 A | 7/1997 |
| JP | 10-046196 A | 2/1998 |
| JP | 10-139654 A | 5/1998 |
| JP | 10120542 A | 5/1998 |
| JP | 10120542 H | 5/1998 |
| JP | 10139654 A | 5/1998 |
| JP | 10-175815 A | 6/1998 |
| JP | 410226642 A | 8/1998 |
| JP | 11346695 A | 12/1999 |
| JP | 2000302678 A | 10/2000 |
| JP | 2000-351720 A | 12/2000 |
| JP | 2001-271096 A | 10/2001 |
| JP | 2004-000019 A | 1/2004 |
| KR | 92-8851 B1 | 10/1992 |
| KR | 92-8853 B | 10/1992 |
| RU | 2066992 C1 | 9/1996 |
| WO | WO 87/07838 A1 | 12/1987 |
| WO | WO 91/04283 A1 | 4/1991 |
| WO | WO 91/07166 A1 | 5/1991 |
| WO | WO 92/09639 A2 | 6/1992 |
| WO | WO 92/09650 A1 | 6/1992 |
| WO | WO 94/06485 A1 | 3/1994 |
| WO | WO 94/07462 A | 4/1994 |
| WO | WO 95/04609 A1 | 2/1995 |
| WO | WO 95/09002 A1 | 4/1995 |
| WO | WO 95/09011 A1 | 4/1995 |
| WO | WO 95/24885 A1 | 9/1995 |
| WO | WO 96/09806 A2 | 4/1996 |
| WO | WO 96/19483 A1 | 6/1996 |
| WO | WO 96/19491 A1 | 6/1996 |
| WO | WO 96/24371 A1 | 8/1996 |
| WO | WO 96/24392 A1 | 8/1996 |
| WO | WO 96/29050 A | 9/1996 |
| WO | WO 96/30035 A1 | 10/1996 |
| WO | WO 96/30396 A1 | 10/1996 |
| WO | WO 96/31194 A2 | 10/1996 |
| WO | WO 96/37497 A1 | 11/1996 |
| WO | WO 96/40121 A1 | 12/1996 |
| WO | WO 96/40199 A1 | 12/1996 |
| WO | WO 97/11033 A2 | 3/1997 |
| WO | WO 97/18904 A1 | 5/1997 |
| WO | WO 97/35998 A1 | 10/1997 |
| WO | WO 97/39733 A1 | 10/1997 |
| WO | WO 98/01107 A1 | 1/1998 |
| WO | WO 98/02134 A1 | 1/1998 |
| WO | WO 98/02138 A1 | 1/1998 |
| WO | WO 98/05333 A1 | 2/1998 |
| WO | WO 98/08503 A1 | 3/1998 |
| WO | WO 98/09987 A1 | 3/1998 |
| WO | WO 98/17246 A1 | 4/1998 |
| WO | WO 98/33089 A1 | 7/1998 |
| WO | WO 98/49153 A1 | 11/1998 |
| WO | WO 99/00110 A1 | 1/1999 |
| WO | WO 99/04752 A2 | 2/1999 |
| WO | WO 99/09065 A1 | 2/1999 |
| WO | WO 99/15917 A1 | 4/1999 |
| WO | WO 99/24003 A1 | 5/1999 |
| WO | WO 99/30729 A1 | 6/1999 |
| WO | WO 99/36050 A1 | 7/1999 |
| WO | WO 99/39682 A2 | 8/1999 |
| WO | WO 99/57178 A1 | 11/1999 |
| WO | WO 00/15188 A1 | 3/2000 |
| WO | WO 00/43049 A1 | 7/2000 |
| WO | WO 00/51554 A2 | 9/2000 |
| WO | WO 00/62740 A2 | 10/2000 |
| WO | WO 00/62741 A2 | 10/2000 |
| WO | WO 00/62743 A2 | 10/2000 |
| WO | WO 00/62744 A2 | 10/2000 |
| WO | WO 00/62745 A2 | 10/2000 |
| WO | WO 00/69404 A1 | 11/2000 |
| WO | WO 00/69406 A1 | 11/2000 |
| WO | WO 00/69407 A1 | 11/2000 |
| WO | WO 00/69408 A1 | 11/2000 |
| WO | WO 00/74699 A | 12/2000 |
| WO | WO 00/76458 A2 | 12/2000 |
| WO | WO 01/029163 A | 4/2001 |
| WO | WO 01/34099 A1 | 5/2001 |
| WO | WO 01/34909 A | 5/2001 |
| WO | WO 01/35920 A1 | 5/2001 |
| WO | WO 02/07697 A | 1/2002 |
| WO | WO 02/07697 A1 | 1/2002 |
| WO | WO 02/064104 A | 8/2002 |
| WO | WO 02/067988 A2 | 9/2002 |
| WO | WO 02/074280 A | 9/2002 |
| WO | WO 03/032941 A | 4/2003 |
| WO | WO 03/039502 A | 5/2003 |
| WO | WO 2004/022024 A | 3/2004 |
| WO | WO 2005/097216 A | 10/2005 |

OTHER PUBLICATIONS

"Avon's Anew Positivity Trio Targets Menopausal Women", The Rose Sheet, Feb. 28, 2000, p. 8.
"CaspACE™ Assay System, Colorimetric", Product Improvements, Neural Notes vol. V, Issue 1, p. 13 (1999) Promega Corporation.
"Elhibin®" Product Brochure, Pentapharm, Centerchem, Inc., Stamford, CT, publicly available prior to Feb. 28, 2001.
"EnzChek® Protease Assay Kits" Product Information, MP06638, pp. 1-4, Revised Feb. 25, 2001, Molecular Probes, Eugene, OR.
"Flavosterone S (Soybean Extract Contained Iso-Flavone", Ichimaru Pharcos Co., Ltd. pp. 11-13 (Dec. 22, 1998).
"Isoral Soybean power makes your skin clear and moist!"—Brochure, publicly available prior to Feb. 28, 2001.
"Lipoxydase Code 411784", Lipoxydase File Apr. 1999, A LIBiol. Body Care Composition.
"Nudit Advertisement", publicly available prior to Feb. 28, 2001.
"Patent Abstracts—Gastric Juice for Antiaging 1997".
"Patent Abstracts—Plant extracts for skin whitening", publicly available prior to Feb. 28, 2001.
"Patent Abstracts—Soybeans for skin pigmentation 1997".
"Patent Abstracts—Soybeans for skin whitening 1997".
"Patent Abstracts of requested patent titles 1996".
"Patent List—Thrombin Inhibitors: List of Relevant Patent Applications as of Jul. 8, 1998, and Oct. 1, 1996."
"Plant Extract Containing Female Hormone-Like Isoflavones—Flavosterone", leaflet from Ichimaru Pharcos issued Mar. 7, 1997.
"Product for Damaged hair by Bristol-Myers-Squibb", (Abstract) publicly available prior to Feb. 28, 2001.
"RQ1 RNase-Free DNASE", Promega Corporation, Technical Bulletin No. 518, pp. 1-4, Feb. 2000, Part#TB518, Promega Corporation. 2800 Woods Hollow Rd., Madison, WI 53711-5399.
"Soy Protein Prevents Skin Tumors From Developing in Mice", *Gene Therapy Weekly*, ISSN 1078-2842, pp. 21 (Nov. 8, 2001).
"Soy Therapy", www.wiseessentials.com/soytherapy.html (email from Jue-Chen Liu, Ph.D. to Cunero et al dated Apr. 13, 2000) Wise Essentials.
"Soybean Technology Improves Skin". *Allured's Cosmetics & Toiletries Magazine*, vol. 115, No. 3, Mar. 2000. p. 22.
"The Joy of Soy", www.wheat-grass.com/851_oral_liquid.shtml, Wheatgrass Express, Inc., 1996.
"ThermoScript™ RNase H-Reverse Transcriptase". Invitrogen™ Life Technologies, www.invitrogen.com/content.cfm, Invitrogen Corporation, 2001.
"Whitening with Soybean? HR has launched "Future White" in Japan", Helena Rubinstein, publicly available prior to Feb. 28, 2001.
Ahrens et al, "Photocarcinogenesis and Inhibition of Intercellular Adhesion Molecular I Expression in Cells of DNA-Repair-Defective Individuals", *Proc. National Academy of Sciences*, vol. 94 (1997) pp. 6837-6841.
Babiarz-Magee et al, "The Expression and Activation of Protease-Activated Receptor-2 Correlate with Skin Color", *Pigment Cell Res*, vol. 17 (2004) pp. 241-251.
Badash et al, "Effect of Gamma Irradiation of Field and Storage Fungi of Wheat, Maize and Soybean", *Chemie Mikrobiologie Technologie der Lebensmittel* (1992).
Balsam et al, Cosmetics, Science and Technology, 2nd Edition, vol. 1, pp. 32-43 (1972).
Balsam et al, Cosmetics, Science and Technology, 2nd Edition, vol. 1, pp. 72-73 (1972).

Barbuch et al, "The Use of Thermospray Liquid Chromatography/Tandem Mass Spectrometry for the Class Identification and Structural Verification of Phytoestrogens in Soy Protein Preparations", *Biomedical and Environmental Mass Spectrometry*, vol. 18 (1989) pp. 973-977.

Barel et al, "Suction Method for Measurement of Skin Mechanical Properties: The Cutometer®", Chapter 14.3, pp. 335-340, *Handbook of Non-Invasive Methods and the Skin*,. Jorgen Serup and G.B.E. Jemec (1995).

Batista et al, "Primary Structure of a Kunitz-Type Trypsin Inhibitor From Enterolobium Contortisiliquum Seeds", *Phytochemistry*, vol. 41, No. 4, (1996) pp. 1017-1022.

Benshimol, "The Biochemistry and Nutrition Group: 30 Years of Research in a Developing Country", *Archivos LatinoAmericanos De Nutrician*, vol. 44, No. 4-S, pp. 6-S-9-S (1994).

Billings et al, "A Growth-Regulated Protease Activity that is Inhibited by the Anticarcinogenic Bowman-Birk Protease Inhibitor", *Pro. Natl. Acad. Sci.*, vol. 89, pp. 3120-3124 (1992).

Birk, "Protein Proteinase Inhibitors in Legume Seeds—Overview", *Archivos Latinoamericanos de Nutricion*, vol. 44, No. 4-S (1994) pp. 26-S-30-S.

Birk, "The Bowman-Birk Inhibitor—Trypsin- and Chymotrypsin-Inhibitor from Soybeans", *Int. J. Peptide Protein Res.*, vol. 25, pp. 113-131 (1985).

Blackheart et al, "Ligand Cross-Reactivity Within the Protease-Activated Receptor Family", *The Journal of Biological Chemistry*, vol. 271, No. 28, pp. 16466-16471 (1996).

Bonifacino et al, "Electrophoresis and Immunoblotting", Chapter 6, pp. 6.0.1-6.6.1, *Current Protocols in Cell Biology*, copyright 2000 by John Wiley & Sons, Inc.

Brass et al, "Protease-Activated G Protein Coupled Receptors on Human Platelets and Endothelial Cells", *F.K. Schattauer Verlagsgesellschaft mbH* (Stuttgart), vol. 78, No. 1, pp. 234-241 (1997).

Chomczynski et al, "Single-Step Method of RNA Isolation by Acid Guanidinium Thiocyanate-Phenol-Chloroform Extraction," *Analytical Biochemistry*, vol. 162, pp. 156-159 (1987).

Clark et al, "Tryptase Inhibitors Block Allergen-induced Airway and Inflammatory Responses in Allergic Sheep", *American Journal of Respiratory and Critical Care Medicine*, vol. 152, pp. 2076-2083, 1995.

Connor et al, "Depletion of Cutaneous Glutathione by Ultraviolet Radiation", *Photochemistry and Photobiology*, vol. 46, No. 2, pp. 239-245 (1987).

Costanzo et al, "Potent Thrombin Inhibitors That Probe the S1 Subsite: Tripeptide Transition State Analogues Based on a Heterocycle Activated Carbonyl Group", *J. Med. Chem.*, vol. 39, 1996, pp. 3039-3043.

Couglin, "Protease Activated Receptors Start a Family", *Proc. Natl. Acad. Sci. USA*, vol. 91, 1994, pp. 9200-9202.

Covelli et al, "Diazepam Inhibits Phagocytosis and Killing Exerted by Polymorphonuclear Cells and Monocytes From Healthy Donors", Abstract, *Immunopharmacology and Immunotoxicology*, vol. 11, No. 4 (1989) pp. 701-714, copyright © 1989 by Marcel Dekker. Inc.

De Seidl, "Interaction of Proteases with Legume Seed Inhibitors, Molecular Features", *Archivos Latinoamericanos de Nutricion*, vol. 44, No. 4-S (1994) pp. 21-S-25-S.

Derian et al, "Differential Regulation of Human Keratinocyte Growth and Differentiation by a Novel Family of Protease-activated Receptors"; *Cell Growth & Differentiation*, vol. 8, pp. 743-749, Jul. 1997.

Dewitt et al, "Astrocytes Regulate Microglial Phagocytosis of Senile Plaque Cores of Alzheimer's Disease", *Experimental Neurology*, vol. 149, Article No. EN976738 (1998) pp. 329-340.

Doolittle, "Proteins", *Reading from Scientific American—The Molecules of Life*, Chapter 4, pp. 38-47 (1985).

Doring, "The Role of Neutrophil Elastase in Chronic Inflammation", *American Journal of Respiratory and Critical Care Medicine*, vol. 150, 1994, pp. S114-S117.

Dunaevsky et al, "Two Groups of Protease Inhibitors Functionally Active in Buckwheat Seeds", soba.shinshu-uac.jp/contents/105.html, publicly available prior to Feb. 28, 2001.

Dunaevsky et al, "Isolation and Properties of Anionic Protease Inhibitors from Buckwheat Seeds", *Biochemistry and Molecular Biology International*, vol. 40, No. 1, (Sep. 1996) pp. 199-208.

Ebling et al, "Hair", *Journal of Investigative Dermatology*, vol. 67, No. 1, pp. 98-105 (Jul. 1976).

Ebling, "Hair Follicles and Associated Glands as Androgen Targets", *Clinics in Endocrinology and Metabolism*, vol. 15, No. 2, pp. 319-339 (May 1986).

Fagerholm et al, "The Effect of a Drug-delivery System Consisting of Soybean Phosphatidyl Choline and Medium-chain Monoacylglycerol on the Intestinal Permeability of Hexarelin in the Rat", *J. Pharm. Pharmacol.* (1998) vol. 50, pp. 467-473.

Fimiani et al, "Mid-Dermal Elastolysis; An Ultrastructural and Biochemical Study", *Arch. Dermatol Res.*, vol. 287, (1995) pp. 152-157.

Fox et al, "Identification of Potential Activators of Proteinase-Activated Receptor-2", *Federation of European Biochemical Societies*, FEBS Letters 417 (1997) pp. 267-269.

Galvez et al, "Chemopreventive Property of a Soybean Peptide (Lunasin) That Binds to Deacetylated Histones and Inhibits Acetylation", *Cancer Research*, vol. 61, No. 20, pp. 7473-7478 (Oct. 15, 2001).

Grant-Theule, "Periodontal Disease, Diabetes, and Immune Response: A Review of Current Concepts", *Peridontal Abstracts*, vol. 44, No. 3, 1996, pp. 69-77.

Greenberger, "Immunologic Aspects of Lung Diseases and Cystic Fibrosis", *JAMA*, vol. 278, No. 22 (1997) pp. 1924-1930.

Guo et al, "A Serine Protease From Suspension-Cultured Soybean Cells", *Phytochemistry*, vol. 47, No. 4 (1998) pp. 547-553.

Hachimi et al, "Do Microglial Cells Phagocyte the B/A4-Amyloid Senile Plaque Core of Alzheimer Diesease?", *C.R. Academy of Science, Paris, Sciences de la vie/Life sciences*, vol. 317, 1994, pp. 445-451.

Hacker, "Common Disorders of Pigmentation—When are more than cosmetic cover-ups required?", *Postgraduate Medicine*, vol. 99, No. 6, 1996, pp. 177-186.

Hafez et al, "Effects of Gamma Irradiation on Proteins and Fatty Acids of Soybean", *Journal of Food Science*, vol. 50 (1985) pp. 1271-1274.

Hamada, "Evaluation of the Effects of Hair Re-growth Agents on Lengthening the Anagen Phase Period and Blockade of Anagen phase-Catagen phase Transformation", *J. Soc. Cosmet. Chem.* Japan, vol. 31, No. 4 (1997) pp. 413-419.

Hanada et al, "Photoprotective Effect of Esterified Glutathione Against Ultraviolet B-Induced Sunburn Cell Formation in the Hairless Mice", *The Journal of Investigative Dermatology*, vol. 108, No. 5, pp. 727-730 (1997).

Hasler et al, "Nutrition Communique, Soy: Just a Hill of Beans?", *Journal of Women's Health*, vol. 7, No. 5 (1998) pp. 519-523.

Hattori et al, "Effects of sup.60 Co- gamma-rays on Defatted Soybean Powder", *Food Irradiation*, vol. 3, No. 1, pp. 104-110 (1968).

Hayashi et al, "Inhibition of Serine Proteases of the Blood Coagulation System by Squash Family Protease Inhibitors", J. Biochem., vol. 116, No. 5, pp. 1013-1018 (1994).

Hendrich et al, "Defining Food Components as New Nutrients", *American Institute of Nutrition*, Food Composition (1994) pp. 1789S-1792S.

Hermanns et al, "Unraveling the Patterns of Subclinical Pheomelanin-Enriched Facial Hyperpigmentation: Effect of Depigmenting Agents", *Dermatology*, vol. 201 (2000) pp. 118-122.

Hoff et al, "Macrophage Uptake of Cholesterol-Containing Particles Derived From LDL and Isolated From Atherosclerotic Lesions". *European Heart Journal*, vol. 11, Supplement E, 1990, pp. 105-115.

Hollenberg et al, "Proteinase-Activated Receptor-2 in Rat Aorta: Structural Requirements for Agonist Activity of Receptor-Activating Peptides", *Molecular Pharmacology*, vol. 49, pp. 229-233 (1996).

Itami et al, "Mechanism of Action of Androgen in Hair Follicles", Journal of Dermatological Science, 7 Suppl., S98-S103 (Jul. 1994).

Jimenez et al, "Mammalian Tyrosinase: Biosynthesis, Processing and Modulation by Melanocyte Stimulating Hormone", *Proc. Natl. Acad. Sci. USA* (1988), vol. 85, pp. 3830-3834.

Jimenez et al, "Specific Identification of an Authentic Clone for Mammalian Tyrosinase", *The Journal of Biological Chemistry*, (1989) vol. 264, No. 6, pp. 3397-3403.

Jingtian et al, "Studies of Soy Sauce Sterlization and its Special Flavour Improvement by Gamma-Ray Irradiation", *Radiation Physics and Chemistry*, vol. 31, Nos. 1-3, pp. 209-213 (1988).

Keeton et al, "The Chemistry of Life", *Biological Science*, Fourth Edition, Chapter 3, pp. 66-67 (1986).

Kennedy et al, "Prevention of Carcinogenesis by Protease Inhibitors", *Cancer Research*, vol. 54, No. 7 (Suppl), pp. 1999s-2005s (Apr. 1, 1994).

Kennedy, "The Evidence for Soybean Products as Cancer Preventive Agents", *The Journal of Nutrition*, vol. 125, No. 3 Suppl, pp. 733s-743s (Mar. 1995).

Kennedy, "Chemopreventive Agents: Protease Inhibitors," *Pharmacol. Ther.*, vol. 78, No. 3, pp. 167-209, 1998, Copyright 1998 Elsevier Science Inc.

Kennedy, "The Bowman Birk Inhibitor from Soybeans As an Anticarcinogenic Agent", *American Journal of Clinical Nutrition*, vol. 68(suppl), pp. 1406S-1412S (1998).

Kovacs et al, "Effect of Irradiation and Dielectric Heating on Soybean Ultrastructure, Trypsin Inhibitor, and Lipoxygenase Activities", *Food Structure*, vol. 10, pp. 217-227 (1991).

Lam et al, "Combined Effect of Irradiation and Dielectric Heating on Chemical Properties of Soybeans", *7th Symp. on Radiation Chemistry*, pp. 477-483 (1990).

Limtrakul et al, "Suppressive Effect of Soybean Milk Protein on Experimentally Induced Skin Tumor in Mice", *Life Sciences*, vol. 53 (1993) pp. 1591-1596.

Liu et al, "Application of Soy in Skin Care", *Journal Nutr.*, vol. 132 (2002) pp. 574S.

Liu et al, "Aqueous Ethanol Extraction of Soybean Trypsin Inhibitors and Characterization of a Calcium-Sensitive Fraction", *Journal of Food Biochemistry*, vol. 15 (1991) pp. 159-168.

Liu, "Chemistry and Nutritional Value of Soybean Components", in *Soybeans, Chemistry, Technology and Utilization*, pp. 32-35 (copyright © 1997 by Chapman & Hall).

MacFarlane et al, "Refractory Periodontitis Associated With Abnormal Polymorphonuclear Leukocyte Phagocytosis and Cigarette Smoking", *J. Peridontal*, vol. 63, No. 11, Nov. 1992, pp. 908-913.

Maes et al, "Leukocytosis, Monocytosis and Neutrophilla: Hallmarks of Severe Depression", *J. Psychiat. Res.*, vol. 26, No. 2 (1992) pp. 125-134.

Mahoney et al, "Amino Acid Sequence and Secondary. Structural Analysis of the Corn Inhibitor of Trypsin and Activated Hageman Factor", *Journal of Biological Chemistry*, vol. 259, No. 13 (Jul. 10, 1984) pp. 8412-8416.

McAdams et al, "Neutrophil and Monocyte Phagocytosis in Depressed Patients", *Prog. Neuro-Psychopharmacol & Biol. Psychiat* (1993) vol. 17, pp. 971-984.

McCutcheon's Emulsifiers and Detergents 1986, North American Edition. McCutcheon Division, Mc Publishing Co., Glen Rock, New Jersey, pp. 317-324 (1986).

Meister, "Glutathione, Ascorbate, and Cellular Protection", *Cancer Research*, vol. 54, pp. 1969s-1975s (1994).

Merck Index (12th Edition), Edited by Susan Budavari (1996) Thrombin., entry 9525, p. 1601.

Merck Index (12th Edition), Edited by Susan Budavari (1996) Trypsin, entry 9926, p. 1669.

Mercola, "Concerns Regarding Soybeans", www.rheumatic.org/soy.htm, publicly available prior to Feb. 28, 2001.

Messina, "Soy Intake and Cancer Risk: A Review of the in Vitro and in Vivo Data", *Nutrician and Cancer*, vol. 21, No. 2 (1994) pp. 113-131.

Mezei et al, "Liposomes-A Selective Drug Delivery System for the Topical Route of Administration: Gel Dosage Form", *Journal of Pharmaceutics and Pharmacology*, vol. 34 (1982), pp. 473-474.

Mezei, "Liposomes as a Skin Drug Delivery System", *Topics in Pharmaceutical Sciences* (D. D. Breimer and P. Speiser, eds.,), Elsevier Science Publishers B. V., New York, N.Y., 1985, pp. 345-358.

Miyagi et al, "Trypsin Inhibitor Activity in Commercial Soybean Products in Japan", *J. Nutr. Sci. Vitaminol* (1997) vol. 43, pp. 575-580.

Molinari et al, "Inhaled Tryptase Causes Bronchoconstriction in Sheep Via Histamine Release", *American Journal of Respiratory and Critical Care Medicine*, vol. 154, pp. 649-653, 1996.

Molino et al. "Interactions of Mast Cell Tryptase with Thrombin Receptors and PAR-2", *Journal of Biological Chemistry*, vol. 272, No. 7, Feb. 14, 1997, pp. 4043-4049.

Morita et al, "Partial Purification and Characterization of a Novel Soybean Protease Which is Inhibited by Kunitz and Bowman-Birk Trypsin Inhibitors", *J. Biochem.*, vol. 119, No. 4, 1996, pp. 711-718.

Mulimani et al, "Effect of Heat Treatments on Trypsin/Chyomotrypsin Inhibitor Activity of Red Gram (*Cajanus cajan* L.)", *Plant Foods for Human Nutrition*, vol. 46, No. 2, (1994) pp. 103-107.

Mulimani et al, "Effects of Heat Treatment and Germination on Trypsin and Chymotrypsin Inhibitory Activities in Sorghum (*Sorghum bicolor* (L.) Moench) Seeds", *Plant Foods for Human Nutrition*, vol. 44, No. 3 (1993) pp. 221-226.

Murphy, "Phytoestrogen Content of Processed Soybean Products", *Food Technology*, vol. 1, pp. 60-64 (1982).

Musclow et al., "Fluorescence Assay to Monitor Phagocytosis by Blood-Clot Derived Polymorphonuclear Leucocytes, 1 Study of Patients With Diabetes and Phagocytosis of Different Staphyloccoccal Species", *Cytobios*, vol. 65, 1991, pp. 15-24 (published and (C) 1991 by the Faculty Press, Cambridge, Great Britain).

Mysliborski et al, "Therapy for Acne Vulgaris", *Comprehensive Therapy*, vol. 7, No. 1, pp. 13-16 (Jan. 1981).

Niemiec et al., "Influence of Nonionic Liposomal Composition on Topical Delivery of Peptide Drugs into Pilosebaceous Units: An in Vivo Study Using the Hamster Ear Model", Pharmaceutical Research, vol. 12, No. 8, 1995, pp. 1184-1188.

Odani et al., "Studies on Soybean Trypsin Inhibitors. XIII. Preparation and Characterization of Active Fragments from Bowman-Birk Proteinase Inhibitor", *Journal Biochem.*, vol. 83, No. 3, pp. 747-753 (1978).

Odani et al., "Wheat Germ Trypsin Inhibitors. Isolation and Structural Characterization of Single-Headed and Double-Headed Inhibitors of the Bowman-Birk Type", *J. Biochem.*, vol. 100, pp. 975-983 (1986).

Orlow et al, "Subcellular Distribution of Tyrosinase and Tyrosinase-Related Protein-1: Implications for Melanosomal Biogenesis", *The Journal of Investigative Dermatology, Inc.*, vol. 100, No. 1, Jan. 1993, pp. 55-64.

Paine et al, "An Alternative Approach to Depigmentation by Soybean Extracts via Inhibition of the PAR-2 Pathway", *Journal Investigative Dermatology*, vol. 116 (2001) pp. 587-595.

Quillien et al, "Trypsin Inhibitor Polymorphism: Multigene Family Expression and Posttranslational Modification", *Journal of Protein Chemistry*, vol. 16, No. 3 (1997) pp. 195-203.

Reiner, "Altered Cell Signaling and Mononuclear Phagocyte Deactivation During Interacellular Infection", *Immunology Today*, vol. 15, No. 8 (1994) pp. 374-381.

Ripka et al, "Chapter 8: Antithrombotics/Serine Protease", Covads International, San Diego, CA, publicly available prior to Feb. 28, 2001.

Robert et al, "Cell-Matrix Interactions in the Genesis of Arteriosclerosis and Alateroma, Effect of Aging", *Laboratorie de Biologie du Tissu Conjonctif*, Annals New York Academy of Sciences, 1992, pp. 331-341.

Santulli et al, "Evidence for the Presence of a Protease-Activated Receptor Distinct from the Thrombin Receptor in Human Keratinocytes", *Proceeding of the National Academy of Sciences USA*, vol. 92, Sep. 1995, pp. 9151-9155.

Scott et al, "Protease-Activated Receptor 2, a Receptor Involved in Melanosome Transfer, is Upregulated in Human Skin by Ultraviolet Irradiation", *Journal Investigative Dermatology*, vol. 117 (2001) pp. 1412-1420.

Scott et al, "Proteinase-Activated Receptor-2 Stimulates Prostaglandin Production in Keratinocytes: Analysis of Prostaglandin Receptors on Human Melanocytes and Effects of PGE2 and PGF2α on Melanocyte Dendricity", *Journal Investigative Dermatology*, vol. 122 (2004) pp. 1214-1224.

Scott et al, "The Proteinase-Activated Receptor-2 Mediates Phagocytosis in a Pho-Dependent Manner in Human Keratinocytes", *Journal Investigative Dermatology*, vol. 121 (2003) pp. 529-541.

Seiberg et al, "Inhibition of Melanosome Transfer Results in Skin Lightening", *Journal Investigative Dermatology*, vol. 115 (2000) pp. 162-167.

Seiberg et al, "Soy Extracts Reduce Hair Growth and Hair Follicle Dimensions", *Hair Science and Technology*, D. Van Neste (editor) (2003) pp. 391-400.

Seiberg et al, "Soymilk Reduces Hair Growth and Hair Follicle Dimensions", *Experimental Dermatology*, vol. 10 (2001) pp. 405-423.

Seiberg et al, "The Protease-Activated Receptor 2 Regulates Pigmentation via Keratinocyte-Melanocyte Interactions", *Experimental Cell Research*, vol. 254 (2000) pp. 25-32.

Seiberg et al, "The Protease-Activated Receptor-2 Regulates Pigmentation via Melanosome Phagocytosis", *Mechanisms of Suntanning*, J. P. Ortonne and R. Ballotti (editors) (2002) pp. 215-278.

Seiberg et al, "The Regulation of Pigmentation by Serine Proteases and Their Inhibitors", Inhibition of Human Proteases: From Target Identification to Therapy, CHI Press (1998) pp. 1-3.

Seiberg et al, "Trypsin-Induced Follicular Papilla Apoptosis Results in Delayed Hair Growth and Pigmentation", *Developmental Dynamics*, vol. 208, pp. 553-564 (1997).

Seiberg, "Keratinocyte-Melanocyte Interactions During Melanosome Transfer", *Pigment Cell Res.*, vol. 14 (2001) pp. 236-242.

Sessa et al, "Toasted Soybean Flour Components with Trypsin Inhibitor Activity", *JAOCS*, vol. 63, No. 6, pp. 784-788 (Jun. 1986).

Setchell, "High-Performance Liquid Chromatographic Analysis of Phytoestrogens in Soy Protein Preparations with Ultraviolet Electrochemical and Thermospray Mass Spectrometric Detection", *Journal of Chromotography*, vol. 386 (1987) pp. 315-323, Chromsymp. 956.

Sharlow et al, "The Protease-Activated Receptor-2 Upregulates Keratinocyte Phagocytosis", *Journal of Cell Science*, vol. 113 (2000) pp. 3093-3101.

Sharpell et al, "Preservation of Cosmetics", Chapter 51, pp. 887-900, Disinfection, Sterilization and Preservation, 4th Edition, Seymour S. Block, Ph. D., Lea & Febiger (1991) publicly available prior to Feb. 28, 2001.

Sligh Jr. et al, "Inflammatory and Immune Responses are Imparied in Mice Deficient in Intercellular Adhesion Molecule 1", *Proc. Natl. Acad., Sci. USA*, vol. 90, 1993, pp. 8529-8533.

Song et al, "PS04.01.44 Crystal Structure of the Complex of Porcine Pancreatic Trypsin with Kunitz-Type Soybean Trypsin Inhibitor", Crystallography of Biological Macromolecules, p. C-106, XVII Congress and General Assembly of the International Union of Crystallog, (1996) (www.bmsc.wahing...ts/abstracts/S0081.html).

Song et al, "Kunitz-Type Soybean Trypsin Inhibitor Revisited: Refined Structure of its Complex with Porcine Trypsin Reveals an Insight into the Interaction Between a Homologous Inhibitor from *Erythrina caffra* and Tissue-type Plasminogen Activator", *J. Mol. Biol.*, vol. 275, pp. 347-363 (1998).

Steenvoorden et al, "Protection Against UV-Induced Reactive Intermediate in Human Cells and Mouse Skin by Glutathione Precursos: A Comparison of N-Acetylcysteine and Glutathione Ethylester", Photochemistry and Photobiology, vol. 67, No. 6, pp. 651-656 (1998).

Steenvoorden et al, "The Use of Endogenous Antioxidants to Improve Photoprotection", *Journal of Photochemistry and Photobiology B: Biology*, vol. 41 (1997) pp. 1-10.

Stenn et al, "Glucocorticoid Effect on Hair Growth Initiation: A Reconsideration," *Skin Pharmacol.*, vol. 6, pp. 125-134 (1993).

Tan-Wilson, "Relevance of Multiple Soybean Trypsin Inhibitor Forms to Nutritional Quality", *Nutritional and Toxicological Significance of Enzyme Inhibitors in Foods*, Edited by Mendel Friedman, Chapter 22, pp. 391-411 (1985), Department of Biological Sciences, State University of New York at Binghamton.

Tashiro et al., "The Complete Amino Acid Sequence of Rice Bran Trypsin Inhibitor", *J. Biochem*, vol. 102, No. 2, pp. 297-306 (1987).

Terada et al, "Amino Acid Sequences of Double-headed Proteinase Inhibitors from the Seeds of *Canavalia lineata*", *Biosci. Biotech. Biochem.*, vol. 58, No. 2, pp. 376-379 (1994).

Thornton et al, "Effect of Androgens on the Growth of Cultured Human Dermal Papilla Cells Derived from Beard and Scalp Hair Follicles", *The Journal of Investigative Dermatology*, vol. 97, No. 2, pp. 345-348 (Aug. 1991).

Travis et al, "The Role of Proteolytic Enzymes in the Development of Pumonary Emphysema and Periodontal Disease", *American Journal of Respiratory and Critical Care Medicine*, vol. 150, 1994, pp. S143-S146.

Tronnier et al., "Adhesion Molecule Expression in Normal Skin and Melanocytic Lesions", *Journal of Cutaneous Pathology*, vol. 24, 1997, pp. 278-285.

Tyrrell et al., "Correlation Between Endogenous Glutathione Content and Sensitivity of Cultured Human Skin Cells to Radiation at Defined Wavelengths in the Solar Ultraviolet Range", *Photochemistry and Photobiology*, vol. 47, No. 3, pp. 405-412 (1988).

Van de Stolpe et al, "Intercellular Adhesion Molecule-1", *J. Mol. Med.*, vol. 74, 1996, pp. 13-33.

Van den Broeke et al, "Topically Applied N-acetylcysteine as a Protector Against UVB-Induced Systemic Immunosuppression", *Journal of Photochemistry and Photobiology, B: Biology*, vol. 27, pp. 61-65 (1995).

Wang et al, "Effects of Soybean Trypsin Inhibitor on Digestive Physiology and Growth and Development of *Helicoverpa armigera* Larvae", *Acta Entomologica Sinica*, vol. 38, No. 3 (Aug. 1995) pp. 272-274.

Webster, "Inflammation in Acne Vulgaris", *Journal of the American Academy of Dermatology*, vol. 33, No. 2, Part 1, 1995, pp. 247-253.

Wiley et al, "Cardiovascular and Renal—Small-molecule direct thrombin inhibitors", Exp. Opin. Ther. Patents, vol. 7, No. 11, 1997, pp. 1265-1282 (Ashley Publications Ltd. ISSN 1354-3776).

Wilson et al, "Immunocytochemical Study of the Interaction of Soybean Trypsin Inhibitor with Rat Intestinal Mucosa", *Gut*, vol. 19 (1978) pp. 260-266.

Xiang et al, "A Study of Nexin 1 of Skin and Hair Follicle during Postnatal Development Period of Rat", Zhongguo Yi Xue Ke Xue Yaun Xue Bao, vol. 20, No. 2, pp. 127-132 (Apr. 1998) Abstract.

Yu et al, "Message of Nexin 1, a Serine Protease Inhibitor, is Accumulated in the Follicular Papilla During Anagen of the Hair Cycle", Journal of Cell Science, vol. 108, Pt 12 (Dec. 1995) pp. 3867-3874 Abstract.

"Superscript II Reverse Transcriptase" protocol published by Gibco-BRL (now Life Tech Inc.) Apr. 1992.

Cunniff, "Official Methods of Analysis of AOAC International", 16th Edition, 5th Revision (1999) AOAC International.

Official Compendia of Standards, USP 24 USP/NF 19, United States Pharmacopeial Convention, Inc. 2000 (Board of Trustees, United States Pharmacopieal Convention, Inc.).

Ogawa, "Current Problem of Research on Hair Growth Mechanisms and Hair Growth Promoters", Fragrace Journal, vol. 5, pp. 1-5 (1989).

Scotti, "Soy-derived Protease Inhibitors Treat Cancer and Inflammation", Windhover Information Inc. (1998).

U.S. Appl. No. 10/611,100, Halas et al.

U.S. Appl. No. 09/110,409, Seiberg et al.

U.S. Appl. No. 10/659,598, Seiberg et al.

U.S. Appl. No. 09/206,249, Seiberg et al.

U.S. Appl. No. 09/677,511, Liu et al.

U.S. Appl. No. 09/621,565, Seiberg et al.

U.S. Appl. No. 10/434,309, Seiberg et al.

U.S. Appl. No. 09/698,454, Seiberg et al.

Ogawa, "Current Problem of Research on Hair Growth Mechanisms and Hair Growth Promoters", Fragrance Journal, vol. 5, pp. 1-5 (1989).

Uniqema: "Pharmaceutical and Cosmetic Uses of Diolic Acids", *Research Disclosure*, Kenneth Mason Publications, Hampshire, GB, vol. 444, No. 77 (Apr. 2001).

Huang et al: "Inhibitory Effect of Topical Applications of Nondenatured Soymilk on the Formation and Growth of UVB-Induced Skin Tumors", *Oncology Research*, vol. 14 (2004) pp. 387-397.

http://familydoctor.org/online/famdocen/home/common/cancer/risk/159.html.

McGuire, "Activation of Epidermal Tyrosinase", *Biochemical and Biophysical Research Communications*, vol. 40, No. 5 (1970) pp. 1084-1089.

Pentapharm, Product "ELHIBIN®" product catalog.

Pentapharm, Product "ELHIBIN®" product catalog (1998).

Wenninger, et al, International Cosmetic Ingredient Dictionary and Handbook, 7th edition, vol. 2 (1997), "Soybean (*Glycine soja*) Protein", p. 1332-1333.

* cited by examiner

COMPOSITIONS AND METHODS FOR TREATING SKIN CONDITIONS

This is a continuation-in-part application of U.S. patent application Ser. No. 09/110,409 filed Jul. 6, 1998 now U.S. Pat. No. 8,039,026, and U.S. patent application Ser. No. 09/698,454 filed Oct. 27, 2000, which are hereby incorporated herein by reference.

FIELD OF THE INVENTION

This invention is related to methods and compositions for treating and ameliorating skin conditions including acne and post inflammatory hyperpigmentation. More particularly, this invention relates to compositions containing salicylic acid, certain natural extracts and natural or synthetic retinoids.

BACKGROUND OF THE INVENTION

Acne is an inflammatory dermatological disorder, which occurs frequently in adolescence and with some regularity in older adults of the human species. The condition of acne can include skin lesions ranging from the comedo in a pilosebaceous follicle, to more severe comedo-inflammatory symptoms such as pustules, papules, cysts and nodules. The condition is not only uncomfortable for the victim, but also embarrassing, and can result in disfigurement and scarring.

The pathology of acne vulgaris is believed to involve a number of factors: the first of which is the formation of comedones more commonly referred to as whiteheads (closed comedones) and blackheads (open comedones). These are solid horny masses that plug follicles and are associated with increased production of sebum. They are made up of tightly packed keratinized cells and sebum. As the comedo enlarges through continued accumulation of keratinized cells, pressure builds up within the follicles which eventually rupture, dumping the contents consisting of horny material, sebum and bacteria into the skin. This provokes inflammatory responses which take the form of pustules (pimples) when the rupture is small and cystic-nodules with complete rupture.

Many different approaches to ameliorating this disorder have been attempted in the past, with some treatments more effective than others. Attacks ranging from simple washing and cleansing to pharmaceuticals have been employed. Agents known and utilized in acne treatment include salicylic acid, the retinoids and retinols. While these agents can significantly improve acne, their undesirable side effects range from mild to severe irritation, redness, peeling, and itching and burning sensation. Thus, it is desired to have a single topical treatment that could prevent or reverse acne with minimal or no undesired side effects.

Aging of the skin is a complex phenomenon resulting from the interaction of several intrinsic and extrinsic factors. Skin changes associated with aging often manifest as cosmetic disabilities. Due to its psychological impact, aging of the skin has become an issue of great social significance and concern. With baby boomers aging, the era of cosmetic care, cosmetic maintenance and rejuvenation gains increased awareness. Methods for preventing and treating skin aging are highly desired. Intrinsic aging is an inevitable, genetically programmed process. Among extrinsic influences (wind, heat, cigarette smoke, chemicals, etc.), ultraviolet radiation appears to be the single most important factor associated with aging of the skin. Photoaging is induced by cumulative exposure to ultraviolet radiation (UVR). Increased recreational sun exposure, including excessive sunbathing, the depletion of stratospheric ozone, and the use of UVR in the treatment of various skin diseases, have led to increased prevalence of photoaging during the last decades. Photodamage can be prevented by sun avoidance and proper sun protection, and could be reversed by the use of topical retinoids, which could be irritating and expensive. Overexposure to ultraviolet and visible radiation also causes sunburn. The use of aspirin and other nonsteroidal anti-inflammatory drugs, cool baths and topical steroids offer only mild relief.

Post inflammatory hyperpigmentation ("PIH") results from healed acne lesions in darkly pigmented individuals. After the acne heals, hyperpigmented spots appear in the area affected by acne lesions. There is a need for a composition that alleviates acne and either prevents or ameliorates PIH.

Various approaches to treating acne, photodamage and other skin conditions have been attempted in the past, including treatment with Vitamin A acid (also known as "tretinoin") and natural retinoids or retinoid precursors such as Vitamin A alcohol (also known as "retinol"). (See U.S. Pat. Nos. 4,877,805 and 4,355,028, for example). However, topical treatment with retinoids can be very irritating to the skin and uncomfortable for the patient. It can cause redness, which may be embarrassing to the patient, particularly those suffering from acne in their teenage years. Oral treatment with retinoids has been found to have teratogenic effects. Thus, it would be desirable to find a topical treatment for acne and PIH.

SUMMARY OF THE INVENTION

In accordance with this invention, we have found compositions and methods for treating and ameliorating acne and PIH containing salicylic acid, nondenatured plant extracts including legume and vegetable extracts having trypsin inhibitory activity and at least one natural or synthetic retinoid or retinol compound.

DETAILED DESCRIPTION OF THE PREFERRED EMBODIMENTS

The compositions of the present invention contain salicylic acid. The amount of salicylic acid may range from about 0.5 percent to about 2 percent by weight, based on the total weight of the composition. The amount of salicylic acid should be high enough to be effective in combating acne disease but not higher than a dose which would irritate a patient's skin.

Preferably, the compositions of this invention contain nondenatured legume or vegetable extracts containing compounds that inhibit trypsin, such as serine protease inhibitors. In particular, nondenatured legume extracts will also be useful in methods of this invention. More preferably, nondenatured soybean, limabean and blackbean extracts, and other natural products made from these beans, such as, but not limited to, bean milk, bean paste, and the like, also serve to reduce pigmentation by this mechanism. Serine protease inhibitors isolated from vegetables or legumes are also useful in this invention, such as, but not limited to, the soybean-derived proteins soybean trypsin inhibitor, "STI" and Bowman-Birk Inhibitor, "BBI".

The novel compositions of this invention preferably contain legume products, and more preferably, soy products, that may be in the form of a fluid (e.g., soymilk) or a solid (e.g., a soybean powder or soymilk powder). What is meant by "soy product" is a substance derived from the soybean, containing the ingredients naturally found in soybeans, at the relative concentrations as found in the beans. What is meant by a "Soy Product" is a substance derived from the soybean. The soy product may contain only a portion of the soybean (e.g., an extract of the soybean such as a lipid reduced soybean powder or filtered soymilk) or may contain the entire soybean (e.g., a ground powder of the legume). The soy product may be in the form of a fluid (e.g., soymilk) or a solid (e.g., a soybean powder or soymilk powder). When in the form of a fluid, the term "soy product" refers to the solid constituents of the fluid that are derived from the soybean.

The soy product may be soybean powder. Soybean powder may be made by grinding dry soybeans. The soybean powder may be lyophilized. Soymilk and soymilk powder are also useful soy products. Soymilk is a combination of solids derived from soybeans and water, the mixture of which has some or all of the insoluble constituents filtered off. Soymilk powder is evaporated soymilk, which in one embodiment, is in a lyophilized or spray-dried form.

Procedures for manufacturing soymilk include, but are not limited to, the following three procedures. First, soymilk may be made by placing soybeans into water to allow them to absorb the water. The swelled beans are then ground and additional water is then added. The mixture may then be filtered to remove any insoluble residue. Second, soymilk may also be prepared from soybean powder. Soybean powder is thoroughly mixed with water (e.g., for at least one hour), which may then be followed by a filtration process to remove insoluble residues. Third, soymilk can also be reconstituted from soymilk powder by adding water. The soymilk may comprise from between about 1% to about 50%, by weight (e.g., from about 5% to about 20%, by weight) of solids from the soybean.

The surface of legume fruits often contain high levels of microorganisms. Thus, prior to use by humans, the legume product needs to be treated to reduce or eliminate such microorganisms.

The legume products utilized in the present invention may have a total microbial content of less than about 10,000 colony-forming units ("cfu") per gram. Preferably, the soy products utilized in the present invention have a microbial content of less than about 1,000 cfu per gram (such as less than about 100 cfu per gram) of the legume product.

The legume products utilized in the present invention may have a total objectionable microbial content of less than 300 cfu per gram such as less than 150 cfu per gram. Preferably, the legume products utilized in the present invention have an undetectable amount of any objectionable microbials for at least one gram (e.g., at least ten grams) of legume product.

The legume product may be exposed to gamma irradiation. The legume product may be exposed to between about 2 to about 30 kGy of gamma irradiation, such as between about 5 and about 10 kGy of gamma irradiation. Such treatment reduces the microbial content of the legume product, while maintaining its biological activity (e.g., serine protease inhibitory activity). The treatment of legume products with gamma irradiation maintains the cosmetic elegance of the legume product, such as maintained natural colors and does not induce significant malodors.

Other anti-microbial processes that also maintain the protease inhibitory activity of the legume product that can be practiced alone or in combination with gamma irradiation, include, but are not limited to, exposure to x-rays, high energy electron or proton beams, ultraviolet radiation, hydrostatic pressure, and addition of chemical agents possessing antimicrobial activity, and combinations thereof.

In one embodiment, the soy product is a non-denatured soy product. "Denaturation" is defined in the Bantam Medical Dictionary (1990 edition) as "the change in the physical and the physiological properties of a protein, that are brought about by heat, X-rays or chemicals. These changes include loss of activity (in the case of enzymes) and loss (or alteration) of antigenicity (in the case of antigens)". What is meant by "non-denatured plant extract" is a product extracted or derived from a plant in which the processing for the derivation of such plant extract (e.g., the temperature, extraction media) did not eliminate its protease inhibitory activity. One such protease is trypsin. In one embodiment, the non-denatured state of the soy product of this invention is measured by the presence of an intact soybean trypsin inhibitor (STI) protein, or by its trypsin inhibitory activity.

The compositions of this invention also contain at least one retinoid (i.e., compounds that bind to any members of the family of retinoid receptors) or retinoid precursor such as retinol, including, for example, tretinoin, retinol, esters of tretinoin and/or retinol, synthetic retinoids such as those set forth in U.S. Pat. No. 4,877,805, for example, and the like. The amount of retinoid in the compositions of the present invention may range from about 0.01 percent to about 1 percent, preferably from about 0.01% percent (the commercial formula has 0.04% retinol) to about 0.5 percent by weight, based on the total weight of the composition.

The compositions of the present invention may contain additional sources of serine protease inhibitors. Additional sources of serine protease inhibitors may be extracted from the species belonging to the following plant families: Solanaceae (e.g., potato, tomato, tomatilla, and the like); Gramineae (e.g., rice, buckwheat, sorghum, wheat, barley, oats and the like); Cucurbitaceae (e.g., cucumbers, squash, gourd, luffa and the like); and, preferably, Leguminosae (e.g., beans, peas, lentils, peanuts, and the like). Ingredients in soy, such as isoflavones, or soy trypsin inhibitor, or non-denatured soy have not previously been known or utilized for reducing retinoid-induced irritation or redness. Surprisingly, we have found that compositions containing such elements are capable of reducing retinoid-induced irritation or redness without affecting retinoid activity.

The compounds which are active in the compositions and methods of this invention may be delivered topically by any means known to those of skill in the art. If the delivery parameters of the topically active pharmaceutical or cosmetic agent so require, the topically active composition of this invention may preferably be further composed of a pharmaceutically or cosmetically acceptable vehicle capable of functioning as a delivery system to enable the penetration of the topically active agent into the skin.

One acceptable vehicle for topical delivery of some of the compositions of this invention, particularly proteins such as trypsin and STI, may contain liposomes. The liposomes are more preferably non-ionic and contain a) glycerol dilaurate (preferably in an amount of between about 5% and about 70% by weight); b) compounds having the steroid backbone found in cholesterol (preferably in an amount of between about 5% and about 45% by weight); and c) one or more fatty acid ethers having from about 12 to about 18 carbon atoms (preferably in an amount of between about 5% and about 70% by weight collectively), wherein the constituent compounds of the liposomes are preferably in a ratio of about 37.5:12.5:33.3:16.7. Liposomes comprised of glycerol dilaurate/cholesterol/polyoxyethylene-10-stearyl ether/polyoxyethylene-9-lauryl ether (GDL liposomes) are most preferred. Preferably the liposomes are present in an amount, based upon the total volume of the composition, of from about 10 mg/mL to about 100 mg/mL, and more preferably from about 20 mg/mL to about 50 mg/mL. A ratio of about 37.5:12.5:33.3:16.7 is most preferred. Suitable liposomes may preferably be prepared in accordance with the protocol set forth in Example 1 of parent application U.S. Ser. No. 09/110,409, though other methods commonly used in the art are also acceptable. The above described composition may be prepared by combining the desired components in a suitable container and mixing them under ambient conditions in any conventional high shear mixing means well known in the art for non-ionic liposomes preparations, such as those disclosed in Niemiec et al., "Influence of Nonionic Liposomal Composition On Topical Delivery of Peptide Drugs Into Pilosebacious Units: An In Vivo Study Using the Hamster Ear Model," 12 Pharm. Res. 1184-88 (1995) ("Niemiec"), which is incorporated by reference herein in its entirety. We have found that the presence of these liposomes in the compositions of this invention may enhance the therapeutic capabilities of some of the compositions of this invention.

Other preferable formulations may contain, for example, soybean milk or other liquid formulations derived directly from legumes or other suitable plant. For example, such a formulation may contain a large proportion of soybean milk, an emulsifier that maintains the physical stability of the soybean milk, and, optionally a chelating agent, preservatives, emollients, humectants and/or thickeners or gelling agents.

Oil-in-water emulsions, water-in-oil emulsions, solvent-based formulations and aqueous gels known to those of skill in the art may also be utilized as vehicles for the delivery of the compositions of this invention.

The topical compositions useful in the present invention involve formulations suitable for topical application to skin. The composition may comprise the soy product and a cosmetically-acceptable topical carrier. The cosmetically-acceptable topical carrier may comprise from about 50% to about 99.99%, by weight, of the composition (e.g., from about 80% to about 95%, by weight, of the composition).

The compositions may be made into a wide variety of product types that include but are not limited to solid and liquid compositions such as lotions, creams, gels, sticks, sprays, shaving creams, ointments, cleansing liquid washes and solid bars, shampoos, pastes, powders, mousses, adhesive strips, and wipes. These product types may comprise several types of cosmetically acceptable topical carriers including, but not limited to solutions, emulsions (e.g., microemulsions and nanoemulsions), gels, solids and liposomes. The following are non-limitative examples of such carriers. Other carriers can be formulated by those of ordinary skill in the art.

The topical compositions useful in the present invention can be formulated as solutions. Solutions typically include an aqueous solvent (e.g., from about 50% to about 99.99% or from about 90% to about 99% of a cosmetically acceptable aqueous solvent).

Topical compositions useful in the subject invention may be formulated as a solution comprising an emollient. Such compositions preferably contain from about 2% to about 50% of an emollient(s) As used herein, "emollients" refer to materials used for the prevention or relief of dryness, as well as for the protection of the skin. A wide variety of suitable emollients are known and may be used herein. See International Cosmetic Ingredient Dictionary and Handbook, eds. Wenninger and McEwen, pp. 1656-61, 1626, and 1654-55 (The Cosmetic, Toiletry, and Fragrance Assoc., Washington, D.C., 7th Edition, 1997) (hereinafter "INCI Handbook") contains numerous examples of suitable materials.

A lotion can be made from such a solution. Lotions typically comprise from about 1% to about 20% (e.g., from about 5% to about 10%) of an emollient(s) and from about 50% to about 90% (e.g., from about 60% to about 80%) of water.

Another type of product that may be formulated from a solution is a cream. A cream typically comprises from about 5% to about 50% (e.g., from about 10% to about 20%) of an emollient(s) and from about 45% to about 85% (e.g., from about 50% to about 75%) of water.

Yet another type of product that may be formulated from a solution is an ointment. An ointment may comprise a simple base of animal or vegetable oils or semi-solid hydrocarbons. An ointment may comprise from about 2% to about 10% of an emollient(s) plus from about 0.1% to about 2% of a thickening agent(s). A more complete disclosure of thickening agents or viscosity increasing agents useful herein can be found in the INCI Handbook pp. 1693-1697.

The topical compositions useful in the present invention may be formulated as emulsions. If the carrier is an emulsion, from about 1% to about 10% (e.g., from about 2% to about 5%) of the carrier comprises an emulsifier(s). Emulsifiers may be nonionic, anionic or cationic. Suitable emulsifiers are disclosed in, for example, INCI Handbook, pp. 1673-1686.

Lotions and creams can be formulated as emulsions. Typically such lotions comprise from 0.5% to about 5% of an emulsifier(s). Such creams would typically comprise from about 1% to about 20% (e.g., from about 5% to about 10%) of an emollient(s); from about 20% to about 80% (e.g., from 30% to about 70%) of water; and from about 1% to about 10% (e.g., from about 2% to about 5%) of an emulsifier(s).

Single emulsion skin care preparations, such as lotions and creams, of the oil-in-water type and water-in-oil type are well-known in the cosmetic art and are useful in the subject invention. Multiphase emulsion compositions, such as the water-in-oil-in-water type are also useful in the subject invention. In general, such single or multiphase emulsions contain water, emollients, and emulsifiers as essential ingredients.

The topical compositions of this invention can also be formulated as a gel (e.g., an aqueous gel using a suitable gelling agent(s)). Suitable gelling agents for aqueous gels include, but are not limited to, natural gums, acrylic acid and acrylate polymers and copolymers, and cellulose derivatives (e.g., hydroxymethyl cellulose and hydroxypropyl cellulose). Suitable gelling agents for oils (such as mineral oil) include, but are not limited to, hydrogenated butylene/ethylene/styrene copolymer and hydrogenated ethylene/propylene/styrene copolymer. Such gels typically comprise between about 0.1% and 5%, by weight, of such gelling agents.

The topical compositions of the present invention can also be formulated into a solid formulation (e.g., a wax-based stick, soap bar composition, powder, or a wipe containing powder).

The topical compositions useful in the subject invention may contain, in addition to the aforementioned components, a wide variety of additional oil-soluble materials and/or water-soluble materials conventionally used in compositions for use on skin, hair, and nails at their art-established levels.

The source of active compound to be formulated will generally depend upon the particular form of the compound. Small organic molecules and peptidyl fragments can be chemically synthesized and provided in a pure form suitable for pharmaceutical/cosmetic usage. Products of natural extracts can be purified according to techniques known in the art. Recombinant sources of compounds are also available to those of ordinary skill in the art.

In alternative embodiments, the topically active pharmaceutical or cosmetic composition may be optionally combined with other ingredients such as moisturizers, cosmetic adjuvants, anti-oxidants, bleaching agents, tyrosinase inhibitors and other known depigmentation agents, surfactants, foaming agents, conditioners, humectants, fragrances, viscosifiers, buffering agents, preservatives, sunscreens and the like.

One of the problems encountered by many individuals who utilize retinoic acid-containing products is increased erythema caused by irritation, a common side effect of retinoid usage. We have found that, surprisingly, the combination of tretinoin and soybean extracts with trypsin inhibitory activity products, such as nondenatured soymilk powder, result in decreased skin redness when applied in combination with or simultaneously with retinoic acid. Preferably, the soy products are utilized in a topical composition containing from about 0.01 to about 50% soybean powder or soymilk powder, more preferably about 0.05 to about 20% soybean powder or soymilk powder and most preferably about 0.5 to about 5% soybean powder or soymilk powder.

The topically active pharmaceutical or cosmetic composition should be applied in an amount effective to reduce retinoid-induced irritation of mammalian skin. As used herein "amount effective" shall mean an amount sufficient to cover the region of skin surface where reduce retinoid-induced irritation is desired. Preferably, the composition is liberally applied to the skin surface such that, based upon a square cm of skin surface, from about 2 µl/cm$^2$ to about 200 µl/cm$^2$ of topically active agent is present when a reduction in irritation or redness is desired.

Natural extracts made directly from plants or botanical sources may be employed in the compositions of this invention in a concentration (w/v) from about 1 to about 99%. Fractions of natural extracts and naturally-derived protease inhibitors such as STI or BBI may have a different preferred range, from about 0.01% to about 20% and, more preferably, from about 0.5% to about 10% of the composition, and most preferably from 0.1% to about 2.5%. Of course, mixtures of the active agents of this invention may be combined and used together in the same formulation, or in serial applications of different formulations.

We have unexpectedly found that when topically active agents are topically applied to an animal's skin, a significant change in skin condition was achieved. Preferably, active agents of this invention are applied to the skin of a mammal at a relatively high concentration and dose (from about 0.005% to about 1% for compounds having high therapeutic indices such as natural and synthetic retinoids and related compounds; from about 20% to about 99% for liquid derivatives and extracts of botanical materials; and from about 0.1% to about 20% for dried extracts or fractions of natural extracts and naturally-derived protease inhibitors such as STI or mixtures thereof) between one and two times daily for a period of time until the skin evidences a change in skin condition. This may be for from about four to about ten weeks or more. Thereafter, once the change in skin condition has been achieved, a lower concentration and dose (from about 0.00001% to about 0.005% for compounds having high therapeutic indices such as natural and synthetic retinoids and related compounds; from about 10% to about 90% for liquid derivatives and extracts of botanical materials; and from about 0.01% to about 5% for fractions of natural extracts and naturally-derived protease inhibitors such as STI or mixtures thereof), of active ingredient may be applied on a less frequent time schedule, e.g., about once per day to about twice per week. The effects of the active agents of this invention are reversible, therefore, in order to maintain these effects, continuous application or administration should be performed. The invention illustratively disclosed herein suitably may be practiced in the absence of any component, ingredient, or step which is not specifically disclosed herein.

Several examples are set forth below to further illustrate the nature of the invention and the manner of carrying it out, but do not serve to limit the scope of the methods and compositions of this invention.

EXAMPLE 1

A composition of the present invention was prepared by combining the ingredients listed in Table 1 below by the process described below Table 1.

TABLE 1

| | INCI Name | Function | % w/w |
|---|---|---|---|
| Water Phase | DI Water | Vehicle | 51.588 |
| | Methyl Gluceth 20 | Humectant | 2.000 |
| | Disodium EDTA | Chelating Agent | 0.100 |
| | Glycerin | Humectant | 1.000 |
| | Ammonium Hydroxide | pH Adjuster | 0.0.46 |
| Oil Phase | C12-C15 Alkyl Benzoate | Emollient | 7.000 |
| | Isoceteth 20 | Solubilizing Agent | 1.375 |
| | PPG 10 Cetyl Ether | Skin Conditioning Agent | 2.200 |
| | Salicylic Acid | Anti-acne Agent | 1.000 |
| | Dimethicone | Skin Conditioning Agent | 2.750 |
| | Phenyl Trimethicone | Skin Conditioning Agent | 0.750 |
| | BHT | Anti-oxidant | 0.100 |
| | Arachidyl Alcohol (and) Behenyl Alcohol (and) Arachidylglucoside | Emulsifier | 3.850 |
| | Cetearyl Alcohol (and) Cetearyl Glucoside | Emulsifier | 4.400 |
| | Cetearyl Alcohol | Emulsifier | 1.400 |
| Post Phase | Polyacrylamide (and) C13-14 Isoparaffin (and) Laureth-7 | Viscosity Increasing Agent | 2.700 |
| Soy Premix 1 | Water | Vehicle | 12.000 |
| | Glycine soja (soybean) Seeds Extracts | Natural Ingredient | 2.000 |
| | Ethylene/Acrylic Acid Copolymer | Skin Conditioning Agent | 0.500 |
| Soy Premix 2 | Glycine soja (soybean) Seeds Extracts | Skin Conditioning Agent | 0.025 |
| | Benzyl Alcohol | Preservative | 0.500 |
| | Methylparaben, Propylparaben, Butylparaben, Ethylparaben & Phenoxyethanol | Preservative | 1.000 |
| | Fragrance | Cosmetic Appeal | 0.300 |
| | Benzalkonium Chloride | Preservative | 0.050 |
| | Retinol | Active | 0.092 |
| | | | 100.000 |

Soy premix 1 was prepared by adding 12 g of deionized water to a glass beaker. *Glycine soja* (soybean) Seeds Extracts (2 g) and Ethylene/Acrylic Acid Copolymer (0.5 g) were added with stirring in between additions.

Soy premix 2 was prepared by combining 0.025 g *Glycine soja* (soybean) Seeds Extracts with 0.5 g benzyl alcohol in a glass beaker and stirring for thirty minutes.

The water phase was prepared in an ESCO VESSEL. To the vessel was added 51.588 g water. Mixing was turned on and the following materials were added: 2 g Methyl Gluceth 20, 0.1 g Disodium EDTA, 1 g Glycerin, and 0.46 g ammonium hydroxide. The solution was heated to 70-75° C.

The oil phase was prepared in a glass beaker by combining the following ingredients while mixing at 75-80° C.: 7 g C12-C15 Alkyl Benzoate, 1.375 g Isoceteth 20, 2.2 g PPG 10 Cetyl Ether, 1 g salicylic acid, 2.75 g DIMETHICONE, 0.75 g phenyl Trimethicone, 0.1 g BHT, 3.85 g Arachidyl Alcohol (and) Behenyl Alcohol (and) Arachidylglucoside, 4.4 g Cetearyl Alcohol (and) Cetearyl Glucoside, and 1.4 g Cetearyl Alcohol. The solution was mixed for 5 minutes, then cooled to 70-75° C. with continued mixing.

The oil phase was slowly added to the water phase with slow to moderate sweep mixing at 70° C. Polyacrylamide (and) C13-14 Isoparaffin (and) Laureth-7 (2.7 g) was added to the solution. The solution was cooled to 45° C. and the soy premix 1 and soy premix 2 were added with stirring. The soy premix vessels were washed with 0.8 g water and the water was added to the solution. The solution was mixed for 10 minutes. The benzalkonium chloride, preservative, and fragrance were added to the solution with 10 minutes stirring between additions. RETINOL. (0.092 g) was added to the solution and stirred for 10 minutes.

EXAMPLE 2

A placebo control was prepared by making a second sample based on the ingredients in Table 1 without the soy derivatives, retinol, and salicylic acid.

Clinical Study

A double-blind, placebo controlled, randomized study was conducted to evaluate the efficacy of a topical formulation of the present invention in improving the appearance of acne and post acne PIH in male and female Asian, African-American and Hispanic subjects with Fitzpatrick Skin Type III-V.

Forty-one Asian, African-American and Hispanic male and female subjects with Skin Type III-V and mild acne vulgaris (10-50 total facial acne lesions), 12 to 45 years of age, completed the double-blind, placebo controlled, randomized, full face, four month long study. Subjects had physically distinct, recent, facial PIH acne marks. Exclusion criteria included subjects using systemic medication within 30 days or topical medication within 14 days before study entry and those who exhibited skin conditions that could interfere with the outcome of the study.

Subjects were provided a composition of the present invention or its placebo based on a randomization scheme. They were asked to apply the test preparation twice on the face, once in the morning and once at night. Subjects were instructed to use a provided facial cleanser and an SPF 15 facial moisturizer throughout the study.

An expert clinical grader assessed global facial acne lesions and target inflammatory lesions as well as skin improvements in facial skin tone and texture. Specific PIH marks were evaluated for darkness, roughness and erythema. Assessments were made at baseline and at various time points throughout the study. The color of the PIH marks was rated on a scale of −1=slightly lighter than pigment of surrounding skin, 0=equal with pigment of surrounding skin, 1=slightly darker than pigment of surrounding skin, 2=moderately darker than pigment of surrounding skin, and 3=extremely darker than pigment of surrounding skin. Post study clinical grading of photos (full face and targeted PIH marks) was carried out to evaluate change in PIH darkness, erythema and size. Additionally, the relative size of the marks was also graded. Each mark was assigned a score of 4 at baseline and graded at subsequent visits using the following scale: 0=PIH mark is not readily visible; 1=PIH mark is 25% of the size of the mark at baseline; 2=PIH mark is 50% of the size of the mark at baseline; 3=PIH mark is 75% of the size of the mark at baseline; and 4=PIH mark is 100% of the size of the mark at baseline.

Subjects were asked to assess various skin attributes at baseline and at various time points throughout the study.

Visible digital photography and Diffuse Reflectance Spectrometer (DRS) measurements were obtained at a wavelength suitable for monitoring melanin concentration. Measurements were taken at baseline and various time points throughout the study. The mark to be monitored was scanned 3 times. Normal skin was also scanned 3 times. The spectra were overlaid and subtracted. Digital Image quantification was carried out for quantification of variables 'L' and 'a'. Variable 'L' refers to luminosity and is measured by the brightness of the measured skin. Variable 'a' measures the redness of the measured skin.

Results

The scores from the clinical grading were averaged and reported as net improvements from baseline. The composition of the present invention showed a significant decrease in darkness, roughness and erythema compared to baseline at week 4 and continued at week 8, 12 and 16 with reduction in darkness seen as early as week 1. Clinical expert grading of photos showed that this composition showed an average % improvements in PIH size of 41% at week 4, 68% at week 8, 82% at week 12 and 92% at week 16. This was statistically significantly more effective than the placebo composition at weeks 4, 8, 12 and 16. This composition was effective on 91% of subjects at week 4 and on 100% of subjects at weeks 8, 12 and 16.

Expert clinical grading showed an average % improvements in PIH darkness of 41% at week 4, 63% at week 8, 80% at week 12 and 92% at week 16. This was statistically significantly more effective than the placebo composition at weeks 8 and 12. This composition was effective on 95% of subjects at week 4 and on 100% of subjects at weeks 8, 12 and 16.

Further statistical analysis of the data also showed that the active composition worked faster than the placebo in reducing the size and darkness of PIH marks.

At one week, target acne lesions exhibited a significant decrease in both erythema and elevation compared to baseline.

Significant improvements were also observed in facial skin tone, texture and global acne assessments compared to baseline.

Digital Image quantification for variable 'L' showed that at weeks 4, 8 and 12, the mean for this composition decreased more appreciably compared with the placebo and there was a trend in favor of the this active composition. Additionally, for variable 'a' the decrease from baseline for the active composition was statistically significant at week 12 for % change in active treatment (27.46% decrease) over the placebo treatment (6.63% increase).

Based on DRS data, the composition of the present invention demonstrated decreases from baseline at each week and the placebo group was equal to baseline or increased from baseline at each week. Subsequent analysis from a subset of population based on baseline melanin content as inclusion criterion indicated a statistically significant decrease for the composition in this invention (0.07 decrease) versus placebo (0.01 decrease) at week 4.

What is claimed is:

1. A method of treating post inflammatory hyperpigmentation comprising topically administering to a mammal in need of treatment therefore an effective amount of a composition comprising (a) from about 0.5 to about 2% by weight of salicylic acid, (b) from about 0.01 to about 1% by weight of a compound selected from the group consisting of synthetic retinoids, natural retinoids, and retinol and (c) from about 0.01 to about 50% by weight of a nondenatured aqueous soybean extract having trypsin-inhibiting activity effective for treating post inflammatory hyperpigmentation.

2. A method according to claim 1 wherein said retinoid is selected from the group consisting of a synthetic retinoid, retinoic acid and retinol.

3. A method according to claim 2 wherein said retinoid is retinol.

4. A method according to claim 1 wherein said soybean extract is in the form of a milk or paste made from said soybean extract wherein said milk or paste is selected from nondenatured soybean milk, nondenatured soybean paste, and mixtures thereof.

5. A method of reducing the darkness of post-inflammatory hyperpigmentation marks on skin comprising applying to said skin a composition according to claim 1.

6. A method of reducing roughness of post-inflammatory hyperpigmentation marks on skin comprising applying to said skin a composition according to claim 1.

7. A method of reducing erythema of post-inflammatory hyperpigmentation marks on skin comprising applying to said skin a composition according to claim 1.

8. A method of reducing the size of post-inflammatory hyperpigmentation marks on skin comprising applying to said skin a composition according to claim 1.

9. A method of treating acne of post-inflammatory hyperpigmentation marks on skin comprising applying to said skin a composition according to claim 1.

10. A composition for treating post inflammatory hyperpigmentation comprising an effective amount of a topical composition comprising (a) from about 0.01 to about 1% by weight of a compound selected from the group consisting of synthetic retinoids, natural retinoids, and retinol, (b) from about 0.5 to about 2% by weight of salicylic acid, and (c) from about 0.01 to about 50% by weight of a nondenatured aqueous soybean extract having trypsin-inhibiting activity.

11. A composition according to claim 10 wherein said retinoid is selected from the group consisting of a synthetic retinoid, retinoic acid and retinol.

12. A composition according to claim 10, wherein said retinoid is retinol.

13. A composition according to claim 10 wherein said soybean extract is in the form of a milk or paste made from said soybean extract wherein said milk or paste is selected from nondenatured soybean milk, nondenatured soybean paste, and mixtures thereof.

* * * * *